United States Patent [19]

Robin et al.

[11] Patent Number: 5,441,990
[45] Date of Patent: Aug. 15, 1995

[54] CLEANED, $H_2$-ENRICHED SYNGAS MADE USING WATER-GAS SHIFT REACTION

[75] Inventors: Allen M. Robin, Anaheim, Calif.; Robert M. Suggitt, Wappingers Falls, N.Y.

[73] Assignee: Texaco Inc., White Plains, N.Y.

[21] Appl. No.: 242,154

[22] Filed: May 13, 1994

Related U.S. Application Data

[63] Continuation of Ser. No. 814,532, Dec. 30, 1991, abandoned.

[51] Int. Cl.6 .......................... C01B 3/12; C01B 3/16; C07C 29/151
[52] U.S. Cl. ...................... 518/703; 252/323
[58] Field of Search .......................... 252/373; 518/703

[56] References Cited

U.S. PATENT DOCUMENTS

| | | | |
|---|---|---|---|
| 3,920,717 | 11/1975 | Marion | 260/449.5 |
| 4,110,359 | 8/1978 | Marion | 260/449.5 |
| 4,202,167 | 5/1980 | Suggitt et al. | 60/39.02 |
| 4,536,382 | 8/1985 | Blytas | 423/437 |
| 4,583,993 | 4/1986 | Chen | 48/197 R |
| 4,597,776 | 7/1986 | Ullman et al. | 48/197 R |
| 4,801,438 | 1/1989 | Najjar et al. | 423/230 |
| 4,946,477 | 8/1990 | Perka et al. | 48/197 R |
| 4,994,093 | 2/1991 | Wetzel et al. | 48/197 R |
| 5,066,476 | 11/1991 | Wetzel et al. | 423/648.1 |

*Primary Examiner*—Howard T. Mars
*Attorney, Agent, or Firm*—Henry H. Gibson

[57] ABSTRACT

Part of CO-rich syngas, including volatile metal or any acid impurities, reacts with water making cleaned, heated, $H_2$-enriched syngas. The rest of the impure CO-rich syngas is combined with hot, $H_2$-enriched syngas making cleaned, $H_2$-rich syngas, useful for making methanol or oxo compounds.

16 Claims, 1 Drawing Sheet

CLEANED, H₂-ENRICHED SYNGAS MADE USING WATER-GAS SHIFT REACTION

This is a continuation of application Ser. No. 07/814,532 filed Dec. 30, 1991, now abandoned.

BACKGROUND OF THE INVENTION

1. Field of the Invention

This invention concerns synthesis gas processing. More particularly, one or more water-gas shift reaction are used to both clean and enrich the hydrogen gas content of $H_2/CO$ mixtures having relatively low hydrogen gas content. The $H_2$-enriched mixtures can be used to make methanol or other oxo compounds.

2. Description of Related Information

Methanol is a significant commodity used in various areas. It can be converted to formaldehyde which is used to make synthetic polymers or to mix with other materials. Methanol is also used to make a wide variety of chemicals including dimethyltoluene, methylamines, chlorinated solvents, acetic acid, isoprene, and so on. Methanol is also increasingly used in fuels. Higher environmental standards and decreasing oil supplies make it likely that methanol demand in fuels will continue to increase in the future.

Gaseous mixtures of hydrogen ($H_2$) and carbon monoxide (CO), known as synthesis gas and commonly called and referred to in this disclosure as syngas, can be used to make methanol ($CH_3OH$) by the chemical reaction shown in Equation 1.

$$CO + 2H_2 = CH_3OH$$

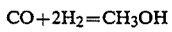

Equation 1. Methanol Synthesis from $H_2/CO$ Mixtures

In addition, syngas typically contains carbon dioxide ($CO_2$) which also reacts with hydrogen to produce methanol, and water, by the chemical reaction shown in Equation 2.

$$CO_2 + 3H_2O = CH_3OH + H_2O$$

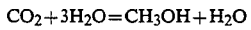

Equation 2. Methanol from $H_2/CO_2$ Mixtures

The stoichiometry for making methanol by reacting hydrogen with carbon monoxide and carbon dioxide, as shown in Equations 1 and 2, requires that more than two moles of hydrogen be added per mole of carbon oxide.

Syngas made from coal or similar carbonaceous material can have a relatively low $H_2/CO$ molar ratio of less than about 1, typically from about 0.5 to about 1. As such, this CO-rich syngas does not have enough hydrogen to make methanol.

The $H_2/CO$ ratio of syngas can be increased by reacting the carbon monoxide with water ($H_2O$), as shown in Equation 3, which is usually called the water-gas shift reaction.

$$CO + H_2O = H_2 + CO_2$$

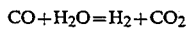

Equation 3. Water-Gas Shift Reaction

For example, U.S. Pat. No. 3,920,717 (Marion) describes methanol production from CO-rich syngas using noncatalytic, thermal, direct, water-gas shift reaction. U.S. Pat. No. 4,946,477 (Perka et al.) describes power generation from CO-rich syngas with combined methanol synthesis using the water-gas shift reaction.

Syngas made from feedstock having nickel, iron or other volatile metals, such as arsenic, can contain volatile metal compounds, including metal carbonyl complexes and arsine ($AsH_3$). Such compounds can poison methanol synthesis or other oxo catalysts and cause problems, such as product contamination and equipment fouling, as well as environmental and disposal concerns. The metal impurities must therefore be removed. U.S. Pat. No. 4,202,167 (Suggitt et al.) discloses one such technique using a water-gas shift reaction of all the syngas, which produces heat, to raise the temperature of the syngas to decompose the metal carbonyl, as well as carbonyl sulfide.

The water-gas shift reaction is a very fast reaction, particularly at higher temperatures and carbon monoxide concentrations typical for CO-rich syngas product streams. Once started, the reaction is hard to control and rapidly reaches equilibrium. Under typical syngas operating conditions, the water-gas shift reaction makes $H_2$-enriched syngas having a $H_2/CO$ ratio of up to about 6, which is much more hydrogen than needed for making methanol. This overly $H_2$-enriched syngas must then be mixed with CO-rich syngas, such as in U.S. Pat. No. 4,110,359 (Marion) disclosing a split stream process for producing syngas used to make methanol. Any metal carbonyl contaminants present in the syngas, however, would pass through the disclosed first gas stream and poison the methanol synthesis catalyst and/or cause other problems, unless more treatment is added. This added purification would increase costs, both for initial investment and for operation, and could still create more problems in disposing of the collected contaminants.

It would therefore be desirable if methanol or other oxo compounds could be made from CO-rich syngas having volatile metal contaminants by raising the $H_2$ content and removing volatile metal contaminants but without requiring added, and expensive, purification procedures or disposal problems.

SUMMARY OF THE INVENTION

This invention concerns processes for making a cleaned, $H_2$-rich $H_2/CO$ mixture comprising three steps. Step (1) involves supplying a CO-rich $H_2/CO$ mixture having a $H_2/CO$ molar ratio of less than about 1 and volatile metal compounds. Step (2) involves separating a part of the CO-rich $H_2/CO$ mixture and reacting CO therein with $H_2O$ to make $CO_2$ and heated, $H_2$-enriched $H_2/CO$ mixture cleaned of volatile metal compounds. Step (3) involves combining the rest of the CO-rich $H_2/CO$ mixture of step (1) with the heated, $H_2$-enriched $H_2/CO$ mixture of step (2) to make heated, recombined $H_2$-rich $H_2/CO$ mixture cleaned of volatile metal compounds.

Partial oxidation reactions are provided comprising three steps. Step (1) involves reacting feedstock containing metal impurities and fluid hydrocarbonaceous fuel and/or solid carbonaceous material with free-oxygen-containing gas through a partial oxidation reaction to make a product stream containing hydrogen and carbon monoxide gases having a $H_2/CO$ molar ratio of less than about 1 and volatile metal compounds. Step (2) involves separating part of the product stream and reacting carbon monoxide therein with water to make heated, $H_2$-enriched product stream. Step (3) involves combining the rest of the product stream of step (1)

with the heated, H$_2$-enriched product stream of step (2) to make heated, recombined H$_2$-rich product stream cleaned of volatile metal compounds.

Processes for making methanol by contacting the H$_2$-rich H$_2$/CO mixture or product stream with methanol catalyst are also provided.

BRIEF DESCRIPTION OF THE DRAWINGS

The accompanying figures show schematic process flowcharts of preferred embodiments of this invention.

DETAILED DESCRIPTION OF THE INVENTION

Figure 1:
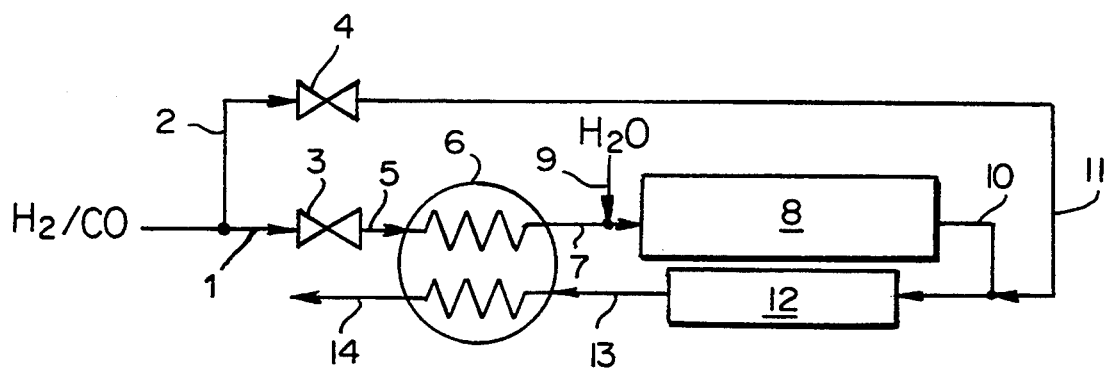

This invention provides a simple, flexible, and direct procedure for producing cleaned, H$_2$-rich syngas, useful in methanol or other oxo compounds synthesis, from CO-rich syngas containing volatile metal contaminants, The procedure can also be designed to retain energy producing value, in the form of chemical potential energy, of the syngas for power generation and to minimize the amount of CO$_2$ formed for more selective sulfide removal from the syngas.

The syngas, meaning mixtures containing hydrogen and carbon monoxide gases, may be made by any, including known, procedure. One source, among others, for making syngas involves a partial oxidation reaction. In the present context, partial oxidation reactions, commonly called gasification, concern the reaction between oxygen and (hydro)carbonaceous feedstock, as set forth in Equation 4, producing primarily hydrogen and carbon monoxide.

$$O_2 + 2HC \rightarrow H_2 + 2CO$$

Equation 4. Partial Oxidation Reaction

In Equation 4, HC represents one or more materials containing hydrogen and carbon from any suitable source, such as hereinafter described. Depending on operating conditions, other reactions can occur, like further oxidation making carbon dioxide, water and so on.

Gasification feedstock may be one or more materials which provide a source of hydrogen and carbon for partial oxidation processes. Fluid hydrocarbonaceous fuel, i.e., a composition comprised of one or more hydrocarbon compounds in a fluid, i.e. gaseous, liquid or fluidized solid state, can be used as feedstock. Typical fluid hydrocarbonaceous fuels include, among others, one or mixtures of the following: petroleum products, including distillates and residues, such as crude petroleum, reduced crude, gasoline, naphtha, kerosine, crude petroleum asphalt, gas oil, residual oil, tar sand oil, shale oil, cycle gas oil, oil derived from coal, lignite, aromatic hydrocarbons (such as benzene, toluene, and xylene fractions), coal tar, furrural extract of coke or gas oil; oxygenated hydrocarbonaceous organic materials including carbohydrates, cellulosics, aldehydes, organic acids, alcohols, ketones, oxygenated fuel oil; waste liquid and by-products from chemical processes containing oxygenated hydrocarbonaceous organic materials; gaseous hydrocarbons and mixtures, including natural gas, refinery offgases or other gas streams containing hydrogen and/or saturated or unsaturated hydrocarbons like methane, ethane, ethene, propane, propene, and so on; waste gases including organic nitrogen, sulfur or oxygen compounds; and other suitable materials.

Another suitable feedstock is solid carbonaceous material, i.e., a composition comprised of one or more solid carbon-containing compounds. Typical solid carbonaceous material includes, among others, one or more of the following: coal, such as anthracite, bituminous, sub-bituminous; coke from coal; lignite, residue derived from coal liquefication; crude residue from petroleum distillation and cracking processes; oil shale; tar sand; petroleum coke; asphalt; pitch; particulate carbon (soot); concentrated sewer sludge: tank and pond bottoms: separator sludge; air flotation solids; and other suitable materials.

Solid carbonaceous material is generally provided in particulate form, such as by grinding preferably to a particle size which passes through an ASTM E11-70 Sieve Designation Standard (SDS) 1.4 mm Alternative No. 14. A suspending medium, such as a slurrying agent, in which the solid feedstock is suspended or entrained may be used. The suspending medium may be any suitable material(s) capable of fluidizing solid feedstock. Typical suspending media include, among others, one of more of the following: water; liquid hydrocarbonaceous material including oxygen-, sulfur- or nitrogen-containing organic liquids; carbon dioxide; steam; nitrogen; recycle synthesis gas; and other suitable materials. The solid carbonaceous material is preferably provided as a pumpable slurry in a slurrying medium. The slurrying medium may be any suitable material, such as water, liquid hydrocarbonaceous material including oxygen-, sulfur- or nitrogen-containing organic liquids, or both. The solids content of solid carbonaceous material in suspending medium may be any suitable amount, typically ranging from about 25 to about 80, preferably from about 45 to about 68, weight percent, depending upon the characteristics of the solid and the suspending medium. The solid carbonaceous material may also be provided as a dry feed, such as fluidized or suspended in a gaseous material such as steam, nitrogen, carbon dioxide, and recycled synthesis gas.

Fluid hydrocarbonaceous fuels and solid carbonaceous materials may be used separately or together and may be combined with any other material. Other material which can be added as feedstock includes any other compounds containing carbon and/or hydrogen including, among others, solid waste material such as garbage and beneficiated garbage, as well as other suitable materials.

The (hydro)carbonaceous and other feedstock usually has at least trace amounts of metal impurities such as, among others, nickel, iron, arsenic, tin, lead and so on.

Free-oxygen-containing gas may be any gas containing oxygen in a form suitable for reaction during the partial oxidation process. Typical free-oxygen-containing gases includes, among others, one of more of the following: air; oxygen-enriched air, i.e., having greater than 21 mole percent oxygen; substantially pure oxygen, i.e. greater than 95 mole percent oxygen; and other suitable material. Commonly, the free-oxygen-containing gas contains oxygen plus other gases derived from the air from which oxygen was prepared, such as nitrogen and rare gases.

Other materials may optionally be added to the gasification process. Any suitable, including known, additives may be provided, such as temperature moderators, fluxing agents, stabilizers, or other useful materials. For example, when using essentially fluid feedstock only it may be necessary or desirable to add an encapsulating agent or other material, such as silica or the like, along with the sorbent to assist slag formation.

Temperature moderators may be desired, such as when the charge includes liquid vaporizable hydrocarbons, in order to simultaneously achieve desired conversion level for optimum efficiency and temperature, such as determined by materials of construction. Typical temperature moderators include, among others, one or more of the following: super-heated steam; saturated steam; water: carbon dioxide-rich gas; cooled exhaust from downstream turbines; by-product nitrogen from an air separation unit; gaseous suspending medium as previously described; and other suitable materials.

Fluxing agents may be added to decrease the viscosity of slag formed during gasification. Any suitable fluxing agent may be used, including, among others, one or more of the following: limestone; iron-containing compounds, including presulfided materials: and other fluxing materials.

Stabilizers and other materials assisting or maintaining feedstock stability or viscosity reduction may be used. Typical stabilizers or viscosity reducing materials include, among others, one or more of the following: anionic surfactants including salts of organic sulfonic acid such as the calcium, sodium and ammonium salts of organic sulfonic acids like liquid sulfonic acid, ammonium lignosulfonate and 2-6-dihydroxy naphthalene sulfonic acid; and other stabilizers.

The proportion of feedstock to free-oxygen-containing gas, as well as any optional components, may be any effective amount sufficient to produce syngas. Typically, the atomic ratio of oxygen, in the free-oxygen-containing gas, to carbon, in the feedstock, is from 0.6 to about 1.6, preferably from about 0.8 to about 1.4. When the free-oxygen-containing gas is substantially pure oxygen, the ratio may be from about 0.7 to about 1.5, preferably about 0.9. When the oxygen-containing gas is air, the ratio may be from about 0.8 to about 1.6, preferably about 1.3. When water or other temperature moderator is used, the weight ratio of temperature moderator to carbon in the feedstock may range up to 2, preferably from about 0.2 to about 0.9, and most preferably about 0.5. The relative proportions of feedstock, oxygen, and any water or other temperature moderator in the feedstreams are carefully regulated to convert a substantial portion of the carbon in the feedstock, generally from about 75 to substantially 100, and preferably from about 80 to about 98, weight percent of the carbon to carbon oxides like carbon monoxide and carbon dioxide, and maintain a suitable autogenous reaction zone temperature.

Carbonaceous or other material which is solid at ambient temperature can be fluidized in any appropriate manner. In the case of some pitches, asphalt, and tar sand, it may be possible to use them as liquids by heating them to temperatures up to their decomposition temperature. Feedstock containing large amounts of water can be pre-dried to a moisture content suitable to facilitate grinding and/or slurrying, such as from about 2 to about 20 weight percent water, depending on the nature of the feedstock. Typically, ground solid carbonaceous or other material is slurried with a slurrying agent in a slurry preparation tank, where the slurry is prepared to a desired concentration, and thereafter pumped to the partial oxidation reactor by means of a slurry feed pump. Alternatively, the ground solid material may be entrained in a gas. When the feedstock is liquid or gaseous, no suspending medium or entraining gas is required.

The partial oxidation reaction is conducted under any suitable reaction conditions, and preferably at the minimum conditions which are effective at converting a desired amount of feedstock to syngas. Temperatures typically range from about 900° C. to about 1650° C., preferably from about 1200° C. to about 1500° C. The pressure in the reaction zone may range from about 1 to about 250, preferably from about 10 to about 200, atmospheres. The time in the reaction zone may range from about 0.5 to about 20, and normally from about 1 to about 5, seconds.

The charge materials, including feedstock, free-oxygen-containing gas and any other materials are delivered to a reactor in which the partial oxidation reaction takes place. Any suitable, including known, means may be used to introduce the feedstock into the reactor. The reactor may include an annulus-type burner, such as described in U.S. Pat. Nos. 2,928,460 (Eastman et al.), 4,328,006 (Muenger et al.) and 4,328,008 (Muenger et al.). Alternatively, the feedstock may be introduced into the upper end of the reactor through a port. Free-oxygen-containing gas is typically introduced at high velocity into the reactor through either the annulus-type burner or a separate port which discharges the oxygen gas directly into the feedstock stream. By this arrangement the charge materials are intimately mixed within the reaction zone and the oxygen gas stream is prevented from directly impinging on the reactor walls. Any suitable, including known, reactor vessel can be used. Typically, a vertical cylindrically shaped steel pressure vessel lined on the inside with a thermal refractory material can be used, such as disclosed in U.S. Pat. Nos. 2,809,104 (Strasser et al.), 2,818,326 (Eastman et al.), 3,544,291 (Schlinger et al.) and 4,637,823 (Dach). The reaction zone typically comprises a downflowing, free-flow, refractory-lined chamber with a centrally located inlet at the top and an axially aligned outlet in the bottom.

Once the charge materials enter the reaction vessel, incomplete combustion takes place in the combustion chamber to give a product stream principally containing hydrogen ($H_2$), carbon monoxide (CO), steam ($H_2O$), and carbon dioxide ($CO_2$). Other gases usually present are hydrogen sulfide ($H_2S$), carbonyl sulfide (COS), methane ($CH_4$), ammonia ($NH_3$), nitrogen ($N_2$), other inert gases such as argon (Ar), and the like. The product stream composition will vary depending upon the composition of the charge materials and reaction conditions. Typically, the product stream contains principal gaseous components and concentrations as follows, given in volume percent on a dry basis, based on using free-oxygen-containing gas which is either substantially pure oxygen or air:

| TYPICAL PRODUCT GAS COMPOSITIONS | | |
|---|---|---|
| Gas | $O_2$ | Air |
| CO | 30–60 | 10–35 |
| $H_2$ | 25–60 | 4–20 |
| $CO_2$ | 2–35 | 2–25 |
| $H_2S$ + COS | 0–5 | 0–3 |
| $N_2$ + Ar | 0–5 | 45–70 |
| $CH_4$ | 0–1 | 0–1 |
| $NH_3$ | 0–0.5 | — |

The product stream leaving the reactor generally has gaseous and non-gaseous by-products, which vary in amount and type depending upon the feedstock composition. When the feedstock includes a solid, such as coal or petroleum coke, the product typically contains particulate ash containing up to about 20, typically from about 1 to about 8, weight percent of the organic carbon in the feed. This particulate ash is entrained in the product gas leaving the reaction zone. During the gasification reaction, partially reacted or unreacted carbonaceous material as well as inorganic material, such as metals and metal compounds derived from the ash portion of the charge, can form a molten slag. Slag is substantially molten ash or molten ash which has solidified into glassy particles. Molten slag accumulates on the vertical walls of the gasifier reactor, and generally flows out of the reactor through an outlet located at the bottom of the reaction zone.

Product stream leaving the reaction zone is generally cooled, by any suitable procedure, to any desired temperature to assist product stream processing and handling. Typically, the product stream is cooled either directly or indirectly by quenching or radiant/convective cooling. In direct cooling by quenching, the product gas is cooled or quenched in a quench vessel, typically located directly below the reactor vessel, by bubbling the product stream through a usually aqueous liquid in the quench vessel. In radiant or indirect cooling, the product stream leaves the reaction zone and enters a radiant or convective cooler, such as through heat exchange surface made up of a series of connected tubes containing water or steam.

The cooled product may be further processed to remove by-product, such as particulates and other impurities. Typically, the cooled product stream passes to a particulate scrubber where the product stream is contacted with aqueous scrubbing liquid to remove particulates entrained in the product stream, as well as further cooling the product stream, to typically from about 150° C. to about 300° C., preferably from about 200° C. to about 250° C., and typically at pressures of from about 2 to about 100, preferably from about 30 to about 70, atmospheres. Particulate matter scrubbed from the product stream may be collected at the bottom of the scrubber and either sent to a clarifier unit, from which the particulates may be recycled as feedstock to the gasification reaction, or may otherwise be disposed of or treated. Scrubbing may be accomplished by any suitable apparatus, including, for example, one or more of the following: spray tower; venturi or jet scrubber; bubble plate contactor; pack column; or other scrubbing apparatus.

When quenching is used, most of the ash, slag and unreacted carbonaceous feedstock is transferred to the water in the quench tank. The pressure in the quench tank is generally the same as the pressure in the gasification reactor, typically located above the quench tank. A portion of the quench water at the bottom of the quench tank may be removed, such as by a lockhopper system and settler as shown in U.S. Pat. No. 3,544,291 (Schlinger et al.). Recovered slag can be isolated and provides a relatively convenient and safe form for disposing of by-products. Glassy slag generally encapsulates any small or trace quantities of toxic or hazardous waste material, like harmful metals, present in the slag, providing long term, stable containment. This residue can have commercial value and may be used as construction material, soil improver, in glass or ceramic manufacturing, or may be sent to a metals reclaiming operation, or other suitable disposal.

Quench and/or scrubbing solutions may be clarified by removing dispersed solids, such as soot and ash, using any suitable, including known, techniques. See, for example, U.S. Pat. No. 4,014,786 (Potter et al.), in which a liquid organic extractant is employed in a decanter system to remove soot from carbon-water dispersions. Alternatively, U.S. Pat. No. 3,544,291 (Schlinger et al.) describes a settler used to separate a stream of clarified water from two water streams of carbon and ash. Once soot and other solids have been removed from quench and/or scrubbing solutions, there may remain in the solution mixtures comprising small amounts of impurities, such as cyanide, metal halides, formates and possibly other by-products of the gasification reaction, such as ammonia and various metals or their corresponding oxides and/or sulfides. To avoid build-up in the recycled water streams, these constituents may be removed by any suitable, including known, techniques, such as disclosed in U.S. Pat. No 4,437,417 (Roberts).

Essentially particle-free product stream leaving the particulate scrubber may be further processed for separating gaseous by-products, if necessary and desired. Water may be removed from the product stream by any effective, including known, means. For example, the product stream may be cooled below the dew point, such as by heat exchange with a coolant, to condense out water. Water can then be separated out in a demoisturing, also called water separation, tank. For example, product stream may be sent to an acid gas separator to remove acid-reacting gases, including sulfur-containing compounds such as $H_2S$ and COS. Any suitable, including known, procedure can be used to remove acid gases, such as disclosed in U.S. Pat. No. 4,781,731 (Schlinger). Cleaned, and optionally dewatered, product stream can be sent on, or stored, for future use.

Small amounts of gaseous by-products are produced, like volatile metal compounds and acid impurities, either during or after the gasification reaction. Metal impurities in the feedstock form metal carbonyl complexes and other volatile metal compounds, such as hydrides, which are stable at high pressures of carbon monoxide and hydrogen typical of syngas processing. For example, metal carbonyls such as nickel tetracarbonyl ($Ni(CO)_4$) and iron pentacarbonyl ($Fe(CO)_5$) are thermodynamically stable at low concentrations in the presence of high partial pressures of carbon monoxide at temperatures up to about 325° C. Such carbonyl complexes are typically formed during cooling or scrubbing procedures when the product stream temperature typically drops to below about 300° C. Acid impurities include hydrogen cyanide, hydrochloric acid, formic acid, acetic acid and so on.

Syngas made from certain (hydro)carbonaceous feedstock, such as coal or other primarily carbonaceous material, has a relatively high proportion of carbon monoxide, characterized as a CO-rich $H_2/CO$ mixture. The relative proportion of hydrogen to carbon monoxide, called the $H_2/CO$ molar ratio, for such CO-rich $H_2/CO$ mixtures is generally less than about 1, usually from about 0.5 to about 1, and most typically about 0.7.

A portion of the CO-rich syngas, such as product stream from a partial oxidation reaction preferably after removing particulates but before separating gaseous by-products, is separated from the remaining CO-rich syngas. The separated portion of CO-rich syngas, having $H_2O$ either present in or added to the product stream, is subjected to a water-gas shift reaction.

The water-gas shift reaction may be conducted using any effective, including known, means for reacting CO with $H_2O$ to make $CO_2$ and $H_2$. The reaction may be conducted in a vessel or other suitable means. Catalyst and/or other materials which assist the reaction may be added. Typical catalysts include, among others, one or mixtures of the following: oxide mixtures such as iron oxide mixed with chromium oxide, with or without promoters including potassium, thorium, uranium, beryllium or antimony: cobalt and molybdenum on a support such as alumina; and the like. Preferred cobalt-molybdenum catalysts have from about 2–5 weight percent cobalt oxide, from about 8–16 weight percent molybdenum trioxide, up to about 20 weight percent magnesium oxide and from about 59 to about 85 weight percent alumina ($Al_2O_3$). The inlet temperature of the CO-rich syngas for the shift reaction will generally be at least about 285° C., and preferably from about 285° C. to about 370° C. The reaction is exothermic such that the temperature increases during the reaction to generally above at least 350° C., and preferably from about 400° C. to about 500° C. The pressure during the reaction is usually at least about 20, preferably from about 34 to about 70, atmospheres.

The exothermic reaction rapidly proceeds to equilibrium which limits the amount of CO reacted due to the high temperatures reached and, depending upon reaction conditions, results in a conversion, for single catalyst bed reactions, of up to 80%, preferably from about 60% to about 75%, and most preferably about 70% of the CO to $CO_2$. This produces an $H_2$-enriched, or shifted, syngas having a $H_2/CO$ molar ratio of at least about 3, preferably from about 3.3 to about 6, and most preferably about 5, but can vary depending on the initial $H_2/CO$ molar ratio and reaction conditions.

Due to the combination of increasing temperature and decreasing CO partial pressure the volatile metal materials decompose to make CO and non-volatile metal material that can be recovered, such as by deposition, including sorption, onto the water-gas shift catalyst or other means.

Carbonyl sulfide (COS) is also hydrolyzed to make hydrogen sulfide and $CO_2$. Similarly, hydrogen cyanide (HCN) is decomposed by hydrolysis to form ammonia and either CO or $H_2$ and $CO_2$. Formic, acetic or other acids present will also decompose by hydrolysis to form hydrogen and $CO_2$. Decomposition of these acid materials further cleans the syngas and increases the life of downstream acid removal means.

Removal of the volatile metal components from the syngas reduces downstream problems including deactivation of any acid gas removal solvent and clogging of acid gas removal means, such as acid gas solvent filters, as well as eliminating the collection of deposits in downstream equipment like heat exchangers, and the deactivation of syngas processing catalysts such as used to make alcohols, like methanol, or other oxo compounds.

The heated, $H_2$-enriched syngas is combined with the remaining, or unshifted, CO-rich syngas to form a heated, recombined, $H_2$-rich syngas stream. The recombined syngas has a $H_2/CO$ molar ratio greater than in the starting CO-rich syngas. The $H_2/CO$ molar ratio of the recombined syngas is generally from about 1.1 to about 3, and preferably from about 1.8 to about 3. When the $H_2$-rich syngas is to be used for methanol production, the $H_2/CO$ molar ratio will preferably be about 2.05.

The recombined syngas is subjected to conditions which act to clean the gas of volatile metal compounds and optionally other gaseous by-products from the unshifted syngas. In one embodiment, the combination of higher temperature and lower CO partial pressure of the recombined syngas causes decomposition of the metal carbonyl complexes. In this embodiment, the temperature of the wet, recombined syngas is at least about 350° C., preferably from about 380° C. to about 450° C., and most preferably from about 415° C. to about 450° C., and the CO concentration is less than about 16, and preferably from about 9 to about 13, volume percent. In this case, the water-gas shift reaction is used not only to clean and increase the $H_2/CO$ molar ratio of the shifted syngas stream but to also clean the unshifted syngas stream. As such, the shifted and unshifted streams are recombined preferably shortly after the water-gas shift reaction and before the shifted syngas is cooled, such as before heat exchange with CO-rich gas fed to the water-gas shift reaction.

In another embodiment, the recombined syngas undergoes another water-gas shift reaction. This second water-gas shift reaction may be conducted under any effective conditions, including conditions similar to those described for the previous water-gas shift reaction, except that the reaction is controlled to convert only a minor portion of CO to $CO_2$. The degree of conversion can be controlled by any effective, including known, means. Typically, the degree of conversion is determined by controlling the inlet temperature, which is the temperature of the syngas upon entering the reactor, using any effective, including known, means, such as a heat exchanger. The degree of conversion may vary depending upon the initial and desired $H_2/CO$ molar ratios. Generally, up to about 25%, preferably from about 10% to about 25%, and most preferably about 10% of the CO is converted to $CO_2$. The degree of conversion is preferably designed to make $H_2$-rich syngas product having a $H_2/CO$ molar ratio equal to or greater than as described previously for the heated, recombined, $H_2$-rich syngas stream.

The cleaned, $H_2$-rich syngas may then be used to generate power through combustion and/or to make methanol or other oxo compounds using any effective, including known, means. The methanol or oxo reaction may be conducted with or without catalyst. Typical catalysts include, among others, one or mixtures of the following: zinc oxide, copper oxide or mixtures thereof, with or without promoter, including mixtures, such as magnesium, aluminum, chromium, iron and manganese; copper-containing catalyst, such as copper oxide and chrome oxide; ternary catalysts of copper, zinc and chromium oxides or of copper, aluminum and zinc; and the like. The reaction may use a single or multibed catalytic reactor, with or without heat exchangers or other means.

The accompanying drawing illustrates preferred embodiments of this invention. FIG. 1 shows an embodiment where CO-rich syngas containing metal contaminants, such as product stream of a partial oxidation reaction of feedstock having metal impurities, is fed partly through each of lines 1 and 2. The relative amount fed through lines 1 and 2 can be controlled by adjusting valves 3 and 4, respectively. The portion of syngas passed through valve 3 is fed through line 5 to a heat exchanger 6 where the syngas is heated by heat exchange with hot, $H_2$-rich syngas. The preheated, CO-rich syngas is passed through line 7 to a water-gas shift reactor 8 containing water-gas shift catalyst. If H$_2$O is needed for the reaction it may be added such as through line 9. CO reacts with H$_2$O in the reactor 8 producing H$_2$, CO$_2$ and heat. Metal contaminants, like nickel or iron carbonyl complexes and arsine, decompose and the metals are deposited on the catalyst. Acid contaminants, like COS, HCN and alkanoic acids, are hydrolyzed. The resulting product is a cleaned, hot, H$_2$-enriched syngas which is passed through line 10. The rest of the CO-rich syngas which is passed through valve 4 is fed through line 11 and combined with the H$_2$-enriched syngas in line 10 to make hot, recombined, H$_2$-rich syngas. Due to the high temperature, generally at or above about 350° C., of the recombined syngas, metal contaminants from the CO-rich syngas decompose and are deposited onto sorbent in filter 12. The cleaned, H$_2$-rich syngas passes through line 13 to heat exchanger 6, as noted previously, and then passes through line 14 for further processing.

Figure 2:
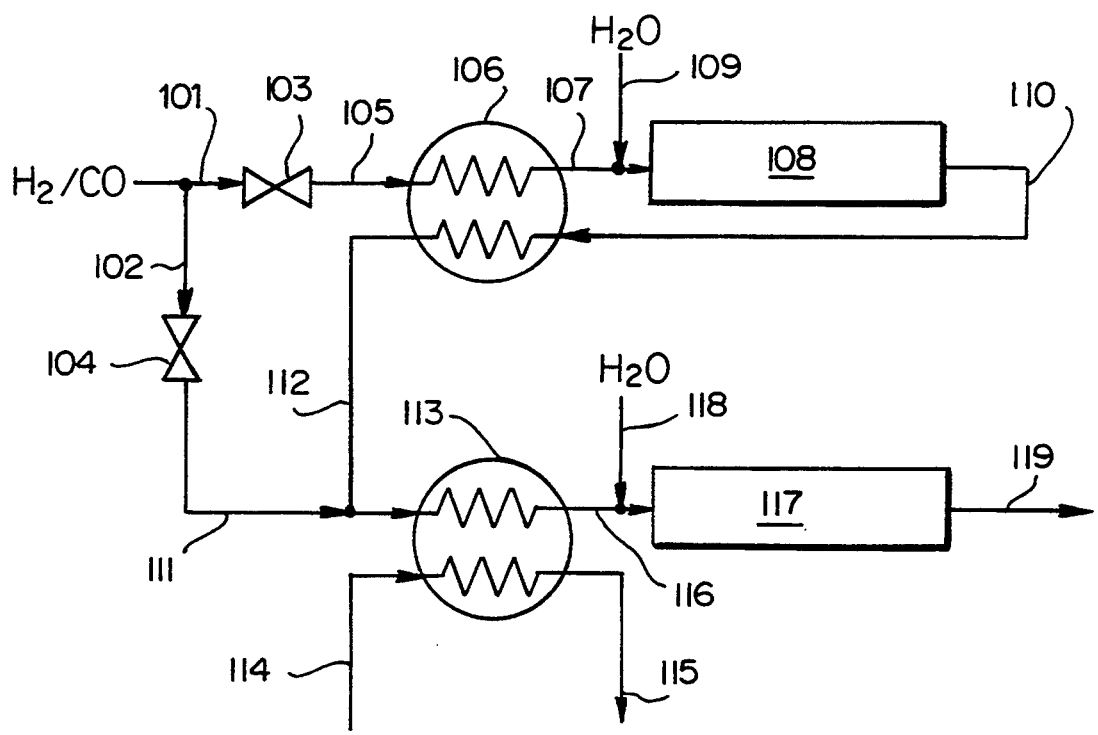

FIG. 2 shows another embodiment where the CO-rich syngas is fed partly through each of lines 101 and 102, and adjusted by valves 103 and 104, respectively. The portion of syngas passed through valve 103 is fed through line 105 to heat exchanger 106 where the syngas is heated by heat exchange with hot H$_2$-enriched syngas. The preheated, CO-rich syngas passes through line 107 to a water-gas shift reactor 108. H$_2$O may be added through line 109, as needed. Cleaned, hot H$_2$-enriched syngas leaves the reactor 108 through line 110. In this embodiment, the syngas in line 110 is passed to heat exchanger 106 to preheat CO-rich syngas, and then passed through line 112 and combined with the rest of the CO-rich syngas from line 111, to form recombined syngas. The recombined syngas is passed to heat exchanger 113, where the temperature of the recombined syngas can be adjusted by heat exchange with a heat transfer fluid, such as steam, introduced to heat exchanger 113 through line 114 and leaving through line 115, to control the rate of conversion of the recombined syngas passed through line 116 in second water-gas shift reactor 117. H$_2$O may be added through line 118, as needed. Part of the CO in the recombined syngas reacts with H$_2$O to make cleaned, H$_2$-rich syngas which passes through line 119 for further processing.

The following examples present illustrative embodiments of this invention without intention to limited scope. All percentages given in the disclosure and claims are in volume percent, unless otherwise stated.

EXAMPLES

Example 1

Single Shift Procedure

This example describes a typical procedure using one water-gas reaction, as shown in FIG. 1. Partial oxidation of Pittsburgh No. 8 Coal makes CO-rich product stream containing hydrogen, carbon monoxide, carbon dioxide and inert gases (generally nitrogen, methane and argon) to which H$_2$O is added during quenching. Typical syngas compositions and reaction conditions are given in Table 1, referring to stream lines shown in FIG. 1, for a CO to CO$_2$ conversion rate of about 75% at a dry gas space velocity of about 4000 hr$^{-1}$ using a cobalt/molybdenum catalyst. About 60% of the CO-rich syngas is fed to the water-gas shift reaction with the remaining 40% recombined after the reaction.

TABLE 1

| SYNGAS COMPOSITION BASED ON FIG. 1 | | | | | |
|---|---|---|---|---|---|
| Line No. | Initial | 2 | 7 | 10 | 13 |
| Moles: | | | | | |
| H$_2$ | 14.7 | 5.9 | 8.8 | 17.9 | 23.8 |
| CO | 20.1 | 8.0 | 12.1 | 3.0 | 11.0 |
| CO$_2$ | 6.0 | 2.4 | 3.6 | 12.7 | 15.1 |
| H$_2$S | 0.4 | 0.2 | 0.2 | 0.2 | 0.4 |
| Inerts | 0.5 | 0.2 | 0.3 | 0.3 | 0.5 |
| COS | 0.01 | 0.004 | 0.006 | nil | nil |
| H$_2$O | 58.3 | 23.3 | 35.0 | 25.9 | 49.2 |
| H$_2$/CO Ratio | 0.73 | 0.73 | 0.73 | 6.0 | 2.16 |
| Temperature | 250° C. | 250° C. | 343° C. | 482° C. | 380° C. |

Example 2

Double Shift Procedure

This example describes a typical procedure using two water-gas shift reactions, as show in FIG. 2, based on a initial syngas composition as in Example 1. In this example, however, the CO-rich syngas is split in half in lines 101 and 102. The first water-gas shift reaction is conducted under conditions similar to those in Example 1, also giving about a 75% conversion. The conversion in the second water-gas shift reactor 117 is controlled to 10% to produce a H$_2$-rich syngas having H$_2$/CO molar ratio of about 2.08.

TABLE 2

| SYNGAS COMPOSITIONS BASED ON FIG. 2 | | | | | | |
|---|---|---|---|---|---|---|
| Line No. | Initial | 107 | 110 | 112 | 116 | 119 |
| Moles: | | | | | | |
| H$_2$ | 14.7 | 7.35 | 14.89 | 14.89 | 22.24 | 23.5 |
| CO | 20.1 | 10.05 | 2.51 | 2.51 | 12.56 | 11.3 |
| CO$_2$ | 6.0 | 3.0 | 10.54 | 10.54 | 13.54 | 14.8 |
| H$_2$S | 0.4 | 0.2 | 0.2 | 0.2 | 0.4 | 0.4 |
| COS | 0.01 | 0.005 | nil | nil | 0.005 | nil |
| Inerts | 0.5 | 0.25 | 0.25 | 0.25 | 0.5 | 0.5 |
| H$_2$O | 58.3 | 29.15 | 21.61 | 21.61 | 50.76 | 49.5 |
| H$_2$/CO Ratio | 0.73 | 0.73 | 5.93 | 5.93 | 1.77 | 2.08 |
| Temperature | 250° C. | 343° C. | 482° C. | 389° C. | 320° C. | 335° C. |

We claim:

1. A process for making a cleaned, H$_2$-rich H$_2$/CO mixture comprising:
   (1) supplying a CO-rich H$_2$/CO mixture having a H$_2$/CO molar ratio of less than about 1 and volatile metal compounds;
   (2) separating part of the CO-rich H$_2$/CO mixture and reacting CO therein with H$_2$O to make CO$_2$ and hot H$_2$-enriched H$_2$/CO mixture cleaned of volatile metal compounds;
   (3) combining the rest of the CO-rich H$_2$/CO mixture of step (1) with the hot, H$_2$-enriched H$_2$/CO mixture of step (2) to make hot, recombined H$_2$-rich H$_2$/CO mixture cleaned of volatile metal compounds.

2. The process of claim 1 wherein the volatile metal compounds are selected from the group consisting of hydrides and carbonyls of arsenic, iron, lead, nickel and tin.

3. The process of claim 1 wherein acid impurities in the CO-rich H$_2$/CO mixture are destroyed by hydrolysis with water in step (2).

4. The process of claim 3 wherein the acid impurities are selected from the group consisting of carbonyl sulfide, hydrogen cyanide, formic acid and acetic acid.

5. The process of claim 1 wherein metals are removed from the H$_2$/CO mixture through deposition onto catalyst used for the reaction in step (2) and by more catalyst or other sorbent after recombining $H_2/CO$ mixtures in step (3).

6. The process of claim 1 wherein part of the CO in the recombined $H_2$-rich $H_2/CO$ mixture of step (3) is reacted with $H_2O$ to make $H_2$-rich $H_2/CO$ mixture having an increased $H_2/CO$ molar ratio of more than 2.

7. A process for making methanol or other oxo compound by contacting the $H_2$-rich $H_2/CO$ mixture of claim 1, following removal of sulfur compounds, with methanol catalyst or oxo catalyst.

8. A partial oxidation reaction comprising:
(1) reacting feedstock, containing metal impurities and either or both fluid hydrocarbonaceous fuel and solid carbonaceous material, with free-oxygen-containing gas through a partial oxidation reaction to make product stream containing hydrogen and carbon monoxide gases having a $H_2/CO$ molar ratio of less than about 1 and volatile metal compounds;
(2) separating part of the product stream and reacting carbon monoxide therein with water to make hot, $H_2$-enriched product stream;
(3) combining the rest of the product stream of step (1) with the hot, $H_2$-enriched product stream of step (2) to make hot, recombined $H_2$-rich product stream cleaned of volatile metal compounds.

9. The process of claim 8 wherein the volatile metal compounds are selected from the group consisting of hydrides and carbonyls of arsenic, iron, lead, nickel and tin.

10. The process of claim 8 wherein acid impurities in the product stream of step (1) are destroyed by hydrolysis with water in step (2).

11. The process of claim 10 wherein the acid impurities are selected from the group consisting of carbonyl sulfide, hydrogen cyanide, formic acid and acetic acid.

12. The process of claim 8 wherein the feedstock contains either or both coal and petroleum residue.

13. The process of claim 8 wherein part of the carbon monoxide in the recombined product stream is reacted with water to make $H_2$-rich product stream having an increased $H_2/CO$ molar ratio of more than 2.

14. A process for making methanol or other oxo compound comprising contacting the $H_2$-rich product stream of claim 8 with methanol or oxo catalyst.

15. The process of claim 1 wherein the hot, recombined $H_2$-rich $H_2/CO$ mixture is at least about 350° C.

16. The process of claim 8 wherein the hot, recombined $H_2$-rich product stream is at least about 350° C.

* * * * *